United States Patent [19]

Sham

[11] Patent Number: 4,826,958

[45] Date of Patent: May 2, 1989

[54] RENIN INHIBITING COMPOUNDS

[75] Inventor: Hing L. Sham, Gurnee, Ill.

[73] Assignee: Abbott Laboratories, Abbott Park, Ill.

[21] Appl. No.: 218,512

[22] Filed: Jul. 1, 1988

Related U.S. Application Data

[63] Continuation of Ser. No. 946,882, Jan. 9, 1987, abandoned, which is a continuation-in-part of Ser. No. 862,077, May 12, 1986, abandoned, which is a continuation-in-part of Ser. No. 801,027, Nov. 22, 1985, abandoned, which is a continuation-in-part of Ser. No. 681,516, Dec. 14, 1984, abandoned.

[51] Int. Cl.$^4$ ............... C07C 103/52; A61K 37/02
[52] U.S. Cl. ............................... 530/331; 530/300; 530/330
[58] Field of Search ............... 530/300, 330, 331; 564/17, 18

[56] References Cited

U.S. PATENT DOCUMENTS

| 4,713,445 | 12/1987 | Szelke et al. | 530/331 |
| 4,721,776 | 1/1988 | Raddatz et al. | 530/331 |
| 4,743,585 | 5/1988 | Hudspeth et al. | 530/331 |
| 4,746,649 | 5/1988 | Raddatz et al. | 530/331 |
| 4,749,781 | 7/1988 | Gordon | 530/331 |
| 4,757,050 | 7/1988 | Natarajan et al. | 530/331 |

OTHER PUBLICATIONS

Boger et al., "Novel Renin Inhibitors Containing the Amino Acid Statine", *Nature*, vol. 303, May 5, 1983, pp. 81–84.
Chemical Abstract, vol 96: 30586v, "New Renin Inhibitors Homologous with Pepstatin", Eid et al.
Chemical Abstract, vol 99: 195414n, "Renin Inhibiting Peptides having Phe Deletion", Boger et al.
Chemical Abstract, vol. 101: 7653c, "Enzyme Inhibitors", Szelke et al.

*Primary Examiner*—John Kight
*Assistant Examiner*—Nathan M. Nutter
*Attorney, Agent, or Firm*—Steven F. Weinstock; Steven R. Crowley; Martin L. Katz

[57] ABSTRACT

The invention relates to renin inhibiting compounds of the formula

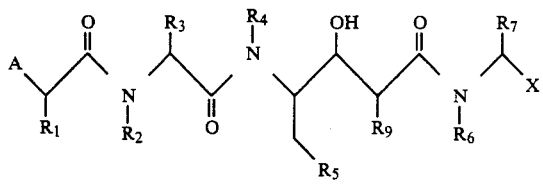

wherein A is

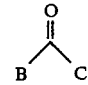

wherein B is thiomorpholino, morpholino, 4-sulfonylmorpholino, 3,4-dihydroxypyrrolidino, alkoxy or loweralkyl and C is NH or $CH_2$; $R_1$, $R_3$ and $R_7$ are independently selected from loweralkyl or lipophilic or aromatic amino acid side chains; $R_2$, $R_4$, and $R_6$ are independently selected from hydrogen or loweralkyl; $R_5$ is phenyl, isopropyl, cyclohexyl, 1,3-dioxan-2-yl; 1,3-dioxolan-2-yl, loweralkyl, 1,3-dithiolan-2-yl or 1,3-dithian-2-yl; X is hydrogen, loweralkyl or —$CH_2OR_8$, wherein $R_8$ is hydrogen, loweralkyl or alkaryl; and $R_9$ is hydrogen, loweralkyl, hydroxy, hydroxyalkyl, difluoro, alkoxy, allyl, alkaryloxy or thioalkyl and pharmaceutically acceptable salts thereof.

10 Claims, No Drawings

RENIN INHIBITING COMPOUNDS

TECHNICAL FIELD

This application is a continuation of application Ser. No. 946,882, filed Jan. 9, 1987, now abandoned, which is a continuation-in-part of U.S. patent application Ser. No. 862,077, filed May 12, 1986 and now abandoned, which is a continuation-in-part of U.S. patent application Ser. No. 801,027 filed Nov. 22, 1985 and now abandoned, which is a continuation-in-part of U.S. patent application, Ser. No. 681,516 filed Dec. 14, 1984 and now abandoned.

The present invention relates to novel compounds and compositions which inhibit renin, and methods of treating hypertensin with such compounds.

BACKGROUND ART

Renin is a proteolytic enzyme synthesized and stored principally in a specific part of the kidney called the juxtaglomerular apparatus. Any of three different physiologic circumstances may cause the release of renin into the circulation: (a) a decrease in the blood pressure entering or within the kidney itself; (b) a decrease in the blood volume in the body; or (c) a fall in the concentration of sodium in the distal tubules of the kidney.

When renin is released into the blood from the kidney, the renin-angiotensin system is activated, leading to vasoconstriction and conservation of sodium, both of which result in increased blood pressure. The renin acts on a circulating protein, angiotensinogen, to cleave out a fragment called angiotensin I (AI). AI itself has only slight pharmacologic activity but, after additional cleavage by a second enzyme, angiotensin converting enzyme (ACE), forms the potent molecule angiotensin II (AII). The major pharmacological effects of AII are vasoconstriction and stimulation of the adrenal cortex to release aldosterone, a hormone which causes sodium retention. AII is cleaved by an aminopeptidase to form angiotensin III (AIII), which compared to AII, is a less potent vasoconstrictor but a more potent inducer of aldosterone release.

Inhibitors of renin have been sought as agents for control of hypertension and as diagnostic agents for identification of cases of hypertension due to renin excess.

With these objectives in mind, the renin-angiotensin system has been modulated or manipulated, in the past, with ACE inhibitors. However, ACE acts on several substrates other than angiotensin I (AI), most notably the kinins which cause such undesirable side effects as pain, "leaky" capillaries, prostaglandin release and a variety of behavioral and neurologic effects. Further, ACE inhibition leads to the accumulation of AI. Although AI has much less vasoconstrictor activity than AII, its presence may negate some of the hypotensive effects of the blockade of AII synthesis.

Inhibition of other targets in the renin-angiotensin system such as AII with compounds such as saralasin can block AII activity, but would leave unimpaired and perhaps enhance the hypertensive effects of AIII.

On the other hand, there are no known side effects which result when renin is inhibited from acting on its substrate. Considerable research efforts have thus been carried out to develop useful inhibitors of renin. Past research efforts have been directed to renin antibodies, pepstatin, phospholipids and substrate analogs such as tetrapeptides and octapeptides to tridecapeptides. These inhibitors either demonstrate poor activity in inhibiting renin production or poor specificity for inhibiting renin only. However, Boger et. al., have reported that statine-containing peptides possess potent and specific renin-inhibiting activity (*Nature*, Vol. 303, p. 81, 1983). In addition, Szelke and co-workers have described polypeptide analogs containing a non-peptide link (*Nature*, Vol. 299, p. 555, 1982) which also cause potent renin inhibition and show a high specificity for this enzyme.

Even with the discovery of such potent renin inhibitors, it has been observed that the more potent renin inhibitors have larger peptide chains but then poorer oral absorption. Conversely, the smaller peptide chain renin inhibiting compounds have shown good oral absorption, but are less potent. Accordingly, to date no renin inhibiting compounds have been found which are both orally active and potent.

DISCLOSURE OF THE INVENTION

In accordance with the present invention, renin inhibiting compounds, which have been found to be both orally active and potent, have the formula

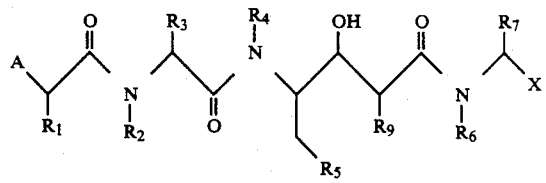

wherein A is

wherein B is thiomorpholino, morpholino, 4-sulfonylmorpholino, 3,4-dihydroxypyrrolidino, alkoxy or loweralkyl and C is NH or $CH_2$; $R_1$, $R_3$ and $R_7$ are independently selected from loweralkyl or lipophilic or aromatic amino acid side chains; $R_2$, $R_4$, and $R_6$ are indepenently selected from hydrogen or loweralkyl; $R_5$ is phenyl, isopropyl, cyclohexyl, 1,3-dioxan-2-yl; 1,3-dioxolan-2-yl, loweralkyl, 1,3-dithiolan-2-yl or 1,3-di-thian-2-yl; X is hydrogen, loweralkyl or —$CH_2OR_8$, wherein $R_8$ is hydrogen, loweralkyl or alkaryl; and $R_9$ is hydrogen, loweralkyl, hydroxy, hydroxyalkyl, difluoro, alkoxy, allyl, alkaryloxy or thioalkyl and pharmaceutically acceptable salts thereof.

The preferable compounds are when $R_2$, $R_4$, $R_6$ and X are hydrogen, $R_1$ is benzyl, α- or β-naphthylmethyl or p-methoxybenzyl; $R_3$ is imidazole-4-yl-methyl, methyl, methylthioethyl, or methylthiomethyl; $R_5$ is isopropyl, cyclohexyl, phenyl, 1,3-dithiolan-2-yl, 1,3-dithian-2-yl, 1,3-dioxolan-2-yl or 1,3-dioxan-2-yl; $R_7$ is isobutyl; $R_9$ is hydrogen, difluoro, propyl, methoxy, alkaryloxy, thioalkyl or allyl and A is t-butyloxycarbonylamino or ethoxycarbonylamino.

The chiral centers of the compounds of the invention may have either the "R" or "S" configuration but preferably have an "S" configuration.

The term "loweralkyl" is used herein refers to straight or branched chain alkyl radicals containing from 1 to 6 carbon atoms including but not limited to methyl, ethyl, n-propyl, isopropyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The term "alkaryl" as used herein refers to an unsubstituted or substituted aromatic ring appended to an alkyl radical including but not limited to benzyl, α- and β-naphthylmethyl, halobenzyl and alkoxybenzyl.

The terms "lipophilic or aromatic amino acid side chains" as used herein refers to those amino acid side chains which have an affinity for lipids or have an aromatic ring and include but are not limited to benzyl, isobutyl, isopropyl, sec-butyl, imidazole-4-yl-methyl, p-hydroxybenzyl, α- and β-naphthylmethyl and cyclohexylmethyl. General reference to amino acid side chains in both the description and claims herein is to be taken as reference to such, whether naturally occurring in proteins or not, and to both D and L-forms.

The term "hydroxyalkyl" as used herein refers to hydroxy-substituted loweralkyl including but not limited to hydroxymethyl.

The term "alkoxy" as used herein refers to substituents of the formula $-OR_{10}$ wherein $R_{10}$ is loweralkyl and includes but is not limited to methoxy.

The term "alkaryloxy" as used herein refers to substituents of the formula $C_6H_5(CH_2)_nO-$ wherein n is 1 to 4 and includes but is not limited to benzyloxy.

The term "thioalkyl" as used herein refers to substituents of formula $-S-R_{11}$ wherein $R_{11}$ is loweralkyl and includes but is not limited to thiomethyl.

The term "allyl" as used herein refers to $H_2C=CH_2CH_2-$.

The terms "Ala", "His", "Leu" and "Phe" as used herein refer to alanine, histidine, leucine and phenylalanine, respectively.

The following Examples will serve to illustrate the novel compounds of the present invention and the preparation thereof.

EXAMPLE 1

4-t-Butyloxycarbonylamino-3-hydroxy-6-methylheptanoic acid ethyl ester

To diisopropylamine (7.7 gm, 0.077 mole) in dry tetrahydrofuran (26 mL) cooled to −20° C. under an argon atmosphere was added dropwise n-butyllithium in hexane (1.46 m, 52.4 mL, 0.077 mole). The solution was stirred 15 minutes, the temperature lowered to −78° C. and dry ethyl acetate (6.7 g. 0.077 mole) added dropwise while maintaining the temperature below −75° C. The solution was stirred 10 minutes and a precooled (−78° C.) tetrahydrofuran solution of Boc-L-leucinal (11 gm., 0.051 mole) was added. After 30 minutes, 2M HCl (40 mL) was added and the mixture was slowly warmed to 10° C. and extracted with ether (3×200 mL). The combined ethereal extract was washed with saturated sodium chloride (NaCl) and dried with magnesium sulfate (MgSO₄) and filtered. Evaporation of the filtrate in vacuo gave 14 gm of crude product which was purified by flash column chromatography (20% ethylacetate in hexane). Obtained 6 gm of Boc-Sta-OEt.

H¹ NMR (300 MHz, CDCl₃, ppm). 0.93 (d, 6H), 1.27 (t, 3H), 1.3–1.75(m, 3H), 1.44(S, 9H), 2.50 (m, 2H), 3.35(S, 1H), 3.63(br m, 1H), 4.03(br m1H), 4.18 (q, 2H), 4.75 (br d, 1H).

EXAMPLE 2

4S-t-Butyloxycarbonylamino-3S-hydroxy-6-methylheptanoic acid (Boc-Statine)

To 0.8 g of Boc-Sta-OEt in 24 mL of dioxane/water (2:1) was added 120 mg of lithium hydroxide at 0° C. After 10 minutes, the mixture was warmed to room temperature. After 1 hour, the mixture was poured to a 10% solution of potassium bisulfate and extracted with ethyl acetate (3×100 mL). The combined organic phase was washed with a saturated NaCl solution and dried with MgSO₄ and filtered. Evaporation of the filtrate in vacuo gave 0.7 g of a white solid. Recrystallization from ether/hexane gave a solid with a m.p. of 117°–118° C.

EXAMPLE 3

Boc-Sta amide of benzyl amine

To a solution of 340 mg of Boc-Sta in 25 mL of tetrahydrofuran at −20° C. was added 183 uL (1.25 eq.) of N-methylmorpholine, followed by 216 uL (1.25 eq.) of isobutylchloroformate. The solution was stirred for 5 minutes at which time 300 uL (excess of benzyl amine was added. After 15 minutes at −20° C., the solution was warmed to 0° C. for 30 minutes. The solid was filtered and the filtrate was evaporated in vacuo. The residual oil was dissolved in ethyl acetate (50 mL) and washed with 10 mL of 10% potassium bisulfate solution. The aqueous phase was extracted with ethyl acetate (2×50 mL) and the combined ethyl acetate solution was washed with saturated NaCl solution and dried with MgSO₄. Evaporation in vacuo gave a colorless oil which upon purification by silca gel column chromatography (5% MeOH/95% CH₂Cl₂) gave 370 mg (82%) of pure product as a colorless oil. Mass spectrum: M+ =364 NMR(60 MHz, CDCl₃, ppm); 0.95 (d, 6H), 1.45 (S, 9H), 1.35–1.55 (m, 3H), 2.4(d, 2H), 3.4–4.4(m, 5H) 4.8(brd, 1H), 6.9 (brd, 1H), 7.25(S, 5H).

EXAMPLE 4

Boc-Sta amide of isobutylamine

Using the procedure of Example 3, but replacing benzylamine with isobutylamine gave the desired compound (87% yield). Mass spectrum: M+ =330.

EXAMPLE 5

Boc-Sta amide of isopentylamine

Using the procedure of Example 3, but replacing benzylamine with isopentylamine gave the desired compound (81% yield). Mass spectrum: M+ =344.

EXAMPLE 6

Boc-Sta amide of 2-methylbutylamine

Using the procedure of Example 3, but replacing benzylamine with 2-methylbutylamine gave the desired compound (86% yield). Mass spectrum: M+ =344.

EXAMPLE 7

Boc-Sta amide of isoleucinol

Using the procedure of Example 3, but replacing benzylamine with isoleucinol gave the desired compound (85% yield). Mass spectrum: M+ =374.

EXAMPLE 8

Boc-Sta amide of methioninol

Using the procedure of Example 3, but replacing benzylamine with methioninol gave the desired compound (83% yield). Mass spectrum: M+ =392.

EXAMPLE 9

Amine hydrochloride of Boc-Sta amide of benzyl amine

Boc-Sta amide of benzylamine (100 mg, 0.27 mmole) was dissolved in 3 mL of 4N HCl and stirred for 10 minutes. The solvent was evaporated in vacuo and the crude product, the amine hydrochloride from deprotection of the N-terminal of Boc-Sta-amide of benzylamine was dried under high vacuum for 12 hours at room temperature. Likewise, the amine hydrochloride of the compounds in Example 4 to Example 7 are prepared by the same procedure.

EXAMPLE 10

Boc-Phe-His-Sta amide of benzylamine

To the amine hydrochloride of Boc-Sta amide of benzylamine (100 mg. 0.34 mmole) in 4 mL of dimethyl formamide (DMF) was added triethylamine (47 uL, 0.34 mmole). The solution was cooled to 0° C.and Boc-Phe-His-OH was added (136 mg, 0.34 mmole), followed by 1-hydroxybenzotriazole (70 mg, 0.51 mmole) and then dicyclohexylcarbodiimide (72 mg, 0.34 mmole). The solution was stirred at 0° C. for 8 hours and then at room temperature for 4 hours. The solution was filtered and the solvent was evaporated under vacuum. The residual solid was dissolved in ethyl acetate (50 mL) and washed with saturated sodium bicarbonate and then saturated sodium chloride solution, dried with $MgSO_4$, filtered and the solvent evaporated in vacuo. The crude product was purified by silica gel column (8% MeOH: 92% $CH_2Cl_2$) and 110 mg. (50%) of product was obtained. m.p. 169°-170° C. Mass spectrum: M+ =648. Anal. calcd. for $C_{35}H_{48}N_6O_6$: C, 64.79; H, 7.46; N, 12.95. Found: C 64.56; H 7.40; N 12.81

EXAMPLE 11

Boc-(α-Naphthyl)-Ala-Ala-Sta amide of benzylamine

To the amine hydrochloride of Boc-Sta amide of benzylamine (100 mg. 0.34 mmole) in THF (3 mL) was added triethylamine (47 uL, 1 equivalent). This solution was added to the mixed anhydride of Boc-(α-Naphthyl)Ala-Ala-OH generated at −20° in the following manner: To Boc-(α-Naphthyl)Ala-Ala-OH (130 mg, 0.34 mmole) in 7 mL of THF at −20° C. was added N-methylmorpholine (0.34 mmole), followed by isobutyl-chloroformate (0.34 mmole). The generation of the mixed anhydride was complete in 5-10 minutes. The reaction mixture was stirred at −20° C. for 2 hours then at 0° C. for 30 minutes. It was poured into a 10% solution of potassium bisulfate (40 mL) and extracted with ethyl acetate (50 mL×3). The combined ethyl acetate solution was washed with saturated sodium bicarbonate (40 mL) and then brine (40 mL), dried with $MgSO_4$ and filtered. The solvent was evaporated in vacuo. The residual oil was purified by silica gel column (5% MeOH:95% $CH_2Cl_2$) to give 140 mg of product (65% yield). M.p. 95°-96° C. Mass spectrum: (M+H)+ =699

EXAMPLE 12

Boc-Phe-His-Sta amide of isobutylamine

Using the procedure of Example 10, but using the amine hydrochloride of Boc-Sta amide of isobutylamine gave the desired compound (60% yield). M.p. 163°-164° C.; Mass spectrum: (M+H)+ =615.

EXAMPLE 13

Boc-(α-Naphthyl)Ala-Ala-Sta-amide of isoleucinol

Using the procedure of Example 11, but using the amine hydrochloride of Boc-Sta amide of isoleucinol gave the desired compound (81% yield). M.p. 181°-182° C.; Mass spectrum: (M+H)+ =643.

EXAMPLE 14

Boc-(α-Naphthyl)Ala-Ala-Sta amide of methioninol

Using the procedure of Example 11, but using the amine hydrochloride of the Boc-Sta amide of methioninol gave the desired product (76% yield). m.p. 183°-184° C.; Mass spectrum: (M+H)+ =661.

EXAMPLE 15

Boc-His-Sta amide of 2-methylbutylamine

Using the procedure of Example 10, but using the amine hydrochloride of Boc-Sta amide of 2-methyl-butylamine and replacing Boc-Phe-His with Boc-His-OH gave the desired compound (60% yield). m.p. 115°-116° C.; Mass spectrum: M+ =481.

EXAMPLE 16 t-Butylacetyl-Phe-His-Sta amide of 2-methylbutylamine

Using the procedure of 11, but using the amine hydrochloride of Example 15 and replacing Boc-(α-Napthyl)-Ala-Ala-OH with t-Butylacetyl-Phe-OH gave the desired compound (45% yield). m.p. 186°-188° C.; Mass spectrum: (M+H)+ =627.

EXAMPLE 17

Boc-p-iodo-Phe-His-Sta amide of 2-methylbutylamine

Using the procedure of Example 11, but using the amine hydrochloride of Example 15 and replacing Boc-(α-Naphthyl)-Ala-Ala with Boc-p-iodo-Phe-OH gave the desired compound (65% yield). m.p. 213° C. (decomp.); Mass spectrum: (M+H)+ =755.

EXAMPLE 18

4S-t-Butyloxycarbonylamino-5-phenyl-3S-hydroxypentanoic acid ethyl ester (Boc-F-Sta ethyl ester)

Using the procedure of Example 1, but replacing Boc-L-leucinal with Boc-L-phenylalaninal gave the desired compound (52% yield). Mass spectrum: M+ =337.

EXAMPLE 19

4S-t-Butyloxycarbonylamino-5-phenyl-3S-hydroxypentanoic acid (Boc-F-Sta)

Using the procedure of Example 2 but using the compound prepared in Example 18 gave the desired compound (95% yield). m.p. 88° C.

EXAMPLE 20

Boc-F-Sta amide of isopentylamine

Using the procedure of example 3, but replacing Boc-Sta with Boc-F-Sta and replacing benzylamine with isopentylamine gave the desired compound (75% yield). m.p. 157°–158° C.; Mass spectrum: M+ =378

EXAMPLE 21

Boc-Phe-His-F-Sta amide of isopentylamine

Using the procedure of Example 10, but using the amine hydrochloride of Boc-F-Sta amide of isopentylamine gave the desired compound (51% yield). m.p. 201°–202° C.; Mass spectrum: (M+H)+ =663.

EXAMPLE 22

4S-t-Butyloxycarbonylamino-3S-hydroxy-5-cyclohexylpentanoic acid ethyl ester (Boc-ACHPA ethyl ester)

Using the procedure of Example 1, but replacing Boc-Leucinal with Boc-Cyclohexylalaninal gave the desired compound in 40% yield. Mass spectrum: M+ =343.

EXAMPLE 23

4S-t-Butyloxycabonylamino-3S-hydroxy-5-cyclohexylpentanoic acid (Boc-ACHPA)

Using the procedure of Example 2, but using the compound from Example 22 gave the desired compound (100% yield). Mass spectrum: M+ =315.

EXAMPLE 24

Boc-ACHPA amide of isopentylamine

Using the procedure of Example 3, but replacing Boc-Sta with Boc-ACHPA and benzyl amine with isopentylamine gave the desired compound (70% yield). Mass spectrum: M+ =384.

EXAMPLE 25

Boc-Phe-His-ACHPA amide of isopentylamine

Using the procedure of Example 10, but using the amine hydrochloride of Boc-ACHPA amide of isopentylamine gave the desired compound (42% yield). m.p. 108°–110° C. Mass spectrum: (M+H)=669.

EXAMPLE 26

4-t-Butyloxycarbonylamino-2-benzyloxy-3-hydroxy-5-cyclohexylpentanoic acid methyl ester Using the procedure of Example 1, but replacing Boc-leucinal with Boc-cyclohexylalaninal, and replacing ethyl acetate with benzyloxymethyl acetate gave the desired compound in 14.5% yield. Mass spectrum: M+ =435.

EXAMPLE 27

4-t-Butyloxycarbonylamino-2-benzyloxy-3-hydroxy-5-cyclohexylpentanoic acid

Using the procedure of Example 2, but using the compound from Example 42 gave the desired compound (100% yield). Mass spectrum: M+ =421.

EXAMPLE 28

4-Boc-amino-2-benzyloxy-3-hydroxy-5-cyclohexylpentanoic acid amide of 2-methylbutylamine Using the procedure of Example 3, but replacing Boc-Sta with the compound prepared in Example 27 and benzyl amine with 2methylbutylamine gave the desired compound (72% yield). Mass spectrum: M+ =490.

EXAMPLE 29

4-Boc-amino-2,3-dihydroxy-5-cyclohexylpentanoic acid amide of 2-methylbutylamine A solution of 400 mg of the compound prepared in Example 28 in 20 mL of methanol with 200 mg of palladium black added was stirred vigorously under 3 atmosphere of hydrogen for 17 hours. The catalyst was filtered off and the solution was concentrated in vacuo. The crude product was purified by silica gel chromatography to give 203 mg (62% yield) of desired product. Mass spectrum: M+ =400.

EXAMPLE 30

Amine hydrochloride of 4-Boc-amino-2-benzyloxy-3-hydroxy-5-cyclohexylpentanoic acid amide of 2-methylbutylamine Using the procedure of Example 9, but replacing Boc-Sta amide of benzylamine with the compound prepared in Example 28 gave the desired product (100% yield).

EXAMPLE 31

Amine hydrochloride of 4-Boc-amino-2,3-dihydroxy-5-cyclohexylpentanoic acid amide of 2-methylbutylamine Using the procedure in Example 9, but replacing Boc-Sta amide of benzylamine with the compound prepared in Example 29 gave the desired product (100% yield).

EXAMPLE 32

Boc-Phe-Alaninyl-4-amino-2-benzyloxy-3-hydroxy-5-cyclohexylpentanoic acid amide of 2-methylbutylamine Using the procedure of Example 11, but replacing Boc-(α-Naphthyl)Ala-Ala-OH with Boc-Phe-Ala-OH and using the amine hydrochloride prepared in Example 30 gave the desired product (59% yield). Mass spectrum: (M+H)+ =709.

EXAMPLE 33

Boc-Phe-Histidinyl-4-amino-2-benzyloxy-3-hydroxy-5-cyclohexylpentanoic acid amide of 2-methylbutylamine Using the procedure of Example 12, but using the amine hydrochloride prepared in Example 30 gave the desired product (40% yield). Mass spectrum: (M+H)+ =776.

EXAMPLE 34

Boc-Phe-Alaninyl-4-amino-2,3-dihydroxy-5-cyclohexylpentanoic acid amide of 2-methylbutylamine Using the procedure of Example 11, but replacing Boc-(α-Naphthyl)Ala-Ala-OH with Boc-Phe-Ala-OH and using the amine hydrochloride prepared in Example 31 gave the desired product. Mass spectrum: (M+H)+ =619.

EXAMPLE 35

Boc-Phe-Histidinyl-4-amino-2,3-dihydroxy-5-cyclohexylpentanoic acid amide of 2-methylbutylamine Using the procedure in Example 11, but using the amine hydrochloride prepared in Example 31 gave the desired product (35% yield). Mass spectrum: $(M+H)^+ = 685$.

EXAMPLE 36

4-t-Butyloxycarbonylamino-2-methoxy-3-hydroxy-5-cyclohexylpentanoic acid ethyl ester Using the procedure of Example 1, but replacing Boc-Leucinal with Boc-cyclohexylalaninal, and replacing ethyl acetate with methoxy ethyl acetate gave the desired product (33% yield). Mass spectrum: $M^+ = 407$.

EXAMPLE 37

4-t-Butyloxycarbonylamino-2-methoxy-3-hydroxy-5-cyclohexylpentanoic acid

Using the procedure of Example 2, but using the compound from Example 36 gave the desired product (100% yield). Mass spectrum: $M^+ = 379$.

EXAMPLE 38

4-Boc-amino-2-methoxy-3-hydroxy-5-cyclohexylpentanoic acid acid amide of 2-methylbutylamine Using the procedure of Example 3, but replacing Boc-Sta with the compound prepared in Example 37 and benzyl amine with 2-methylbutylamine gave the desired product (80% yield). Mass spectrum: $(M+H)^+ = 449$.

EXAMPLE 39

Amine hydrochloride of 4-Boc-amino-2-methoxy-3-hydroxy-5-cyclohexylpentanoic acid amide of 2-methylbutylamine Using the procedure of Example 9, but replacing Boc-Sta amide of benzyl amine with the compound prepared in Example 38 gave the desired compound (100% yield).

EXAMPLE 40

Boc-Phe-Histidinyl-4-amino-2-methoxy-3-hydroxy-5-cyclohexylpentanoic acid amide of 2-methylbutylamine Using the procedure of Example 10, but using the amine hydrochloride prepared in Example 39 gave the desired product (35% yield). Mass spectrum: $(M+H)^+ = 699$.

EXAMPLE 41

4-t-Butyloxycarbonylamino-2-allyl-3-hydroxy-5-cyclohexylpentanoic acid ethyl ester Using the procedure of Example 1, but replacing Boc-Leucinal with Boc-cyclohexylalaninal, and replacing ethyl acetate with ethyl-4-pentenoate gave the desired product in 55% yield. Mass spectrum: $M^+ = 383$.

EXAMPLE 42

4-t-Butyloxycarbonylamino-2-allyl-3-hydroxy-5-cyclohexylpentanoic acid

Using the procedure of Example 2, but using the compound from Example 41 gave the desired compound (100% yield). Mass spectrum: $M^+ = 355$.

EXAMPLE 43

4-Boc-amino-2-allyl-3-hydroxy-5-cyclohexylpentanoic acid amide of 2-methylbutylamine Using the procedure of Example 10, but replacing Boc-Phe-His-OH with the compound prepared in Example 42 and using 2-methylbutylamine instead of an amine hydrochloride gave the desired product (50% yield). Mass spectrum: $M^+ = 424$.

EXAMPLE 44

Amine hydrochloride of 4-t-Boc-amino-2-allyl-3-hydroxy-5-cyclohexylpentanoic acid amide of 2-methylbutylamine Using the procedure of Example 13, but replacing Boc-Sta amide of benzylamine with the compound prepared in Example 59 gave the desired compound (100% yield).

EXAMPLE 45

Boc-Phe-Histidinyl-4-amino-2-allyl-3-hydroxy-5-cyclohexylpentanoic acid amide of 2-methylbutylamine Using the procedure of Example 10, but using the amine hydrochloride prepared in Example 44 gave the desired product (40% yield). Mass spectrum: $(M+H)^+ = 709$.

EXAMPLE 46

Boc-Phe-Histidinyl-4-amino-2-propyl-3-hydroxy-5-cyclohexylpentanoic acid amide of 2-methylbutylamine A solution of 11 mg of the compound of Example 45 in methanol with 3 mg of 10% palladium on charcoal added was stirred vigorously under hydrogen atmosphere for 2 hours at room temperature. The catalyst was filtered off and the filtrate concentrated to give a colorless oil. Purification by silica gel column chromatography gave 11 mg of pure product (100% yield). Mass spectrum: $(M+H)^+ = 711$.

EXAMPLE 47

Boc-Phe-Methioninyl-4-amino-2-methoxy-3-hydroxy-5-cyclohexylpentanoic acid amide of 2-methylbutylamine Using the procedure of Example 11, but replacing Boc-(α-Naphthyl)-Ala-Ala-OH with Boc-Phe-Met-OH and using the amine hydrochloride prepared in Example 39 gave the desired compound (80% yield). Mass spectrum: $(M+H)^+ = 693$.

EXAMPLE 48

Boc-Phe-S-methylcysteinyl-4-amino-2-methoxy-3-hydroxy-5-cyclohexlpentanoic acid amide of 2-methylbutylamine Using the procedure of Example 11, but replacing Boc-(α-Naphthyl)-Ala-Ala-OH with Boc-Phe-S-methylcysteine and using the amine hydrochloride prepared in Example 39 gave the desired compound (63% yield). Mass spectrum: $(M+H)^+ = 679$.

EXAMPLE 49

Boc-Phe-Alaninyl-4-amino-2-allyl-3-hydroxy-5-cyclohexylpentanoic acid amide of 2-methylbutylamine Using the procedure of Example 11, but replacing Boc-(α-Naphthyl)-Ala-Ala-OH with Boc-Phe-Ala-OH and using the amine hydrochloride prepared in Example 44 gave the desired compound (56% yield). Mass spectrum: (M+H)+ =643.

EXAMPLE 50

Boc-Phe-S-methylcysteinyl-4-amino-2-allyl-3-hydroxy-5-cyclohexylpentanoic acid amide of 2-methylbutylamine Using the procedure of Example 11, but replacing Boc-(α-Naphthyl)-Ala-Ala-OH with Boc-Phe-S-methylcysteine and using the amine hydrochloride prepared in Example 44 gave the desired compound (52% yield). Mass spectrum: (M+H)+ =689.

EXAMPLE 51

2S-Benzyloxycarbonylamino-1,4S-butanediol

To 15 g of N-benzyloxycarbonyl L-aspartic acid in 250 mL of tetrahydrofuran at 0° C. was added two equivalents of $BH_3 \cdot THF$ (1M). The solution was stirred at 0° C. for 30 minutes and then at room temperature for 3.5 hours. The reaction was carefully quenched with cold water. The product was extracted with ethyl acetate (3×300 mL) and the combined organic phase washed with brine and dried with anhydrous $MgSO_4$. Filtration and concentration gave an oil which was purified by silica gel column chromatography (10% $MeOH/CH_2Cl_2$) to give 7.1 g of white solid. Mass spectrum: M+ =239.

EXAMPLE 52

4-Hydroxyethyl-oxazolidin-2-one

To 1.1 g of the compound in Example 51 in 25 mL of DMF at 0° C. was added 360 mg of sodium hydride (60% oil dispersion) portionwise. At the end of the addition, the suspension was stirred at 0° C. for 2 hours and then at room temperature overnight. The solvent was evaporated under reduced pressure. The crude oily product was purified by silica gel column chromatography (10% $MeOH/CH_2Cl_2$) to give 580 mg of white solid, m.p. 90°–91° C. Mass spectrum: M+ =131.

EXAMPLE 53

(Oxazolidin-2-one-4-yl)ethanal

To 520 mg of the product from Example 52 in 110 mL of $CH_2Cl_2$ was added 2.1 g of pyridinium dichromate. The suspension was stirred at room temperature overnight. The reaction mixture was filtered through a tightly packed layer of celite and concentrated under reduced pressure. The crude brown oil was purified by silica gel column chromatography (5% $MeOH/CH2Cl2$) to give 270 mg of pure aldehyde. Mass spectrum: M+ =129.

EXAMPLE 54

4S-[(1',3'-Dithiolan-2'-yl)methyl]oxazolidin-2-one

To a solution of 370 mg of the aldehyde from Example 53 in 30 mL of dichloromethane was added 0.48 mL of 1,2-ethanedithiol. To this solution at 0° C. was added 2 drops of boron trifluoride-ether complex. The solution was stirred at 0° C. for 10 minutes and then at room temperature for 20 minutes. TLC analysis showed no aldehyde was left. The solution was concentrated and the crude oily residue was purified by silica gel column chromatography ($CH_2Cl_2$/EtOAc 1:1) to give 270 mg of product. Mass spectrum: M+ =205.

EXAMPLE 55

4S-[(1',3'-Dithian-2'-yl)methyl]oxazolidin-2-one

Using the procedure of Example 54, replacing 1,2-ethanedithiol with 1,3-propane-dithiol gave the desired product (70%). Mass spectrum: M+ =219.

EXAMPLE 56

4S-[(1',3'-Dioxolan-2'-yl)methyl]oxazolidin-2-one

To 320 mg of the aldehyde from Example 53 in 25 mL of benzene was added 1 mL of ethylene glycol and 10 mg of p-toluenesulfonic acid. The solution was heated to reflux for one hour and cooled to room temperature. It was washed with saturated sodium bicarbonate solution and extracted with ethyl acetate (3×50 mL). The organic phase was dried with anhydrous $MgSO_4$, filtered and concentrated under reduced pressure. Purification of the crude product by silica gel column chromatography (5% $MeOH/CH_2Cl_2$) gave 213 mg of the desired product. Mass spectrum: M+ =173.

EXAMPLE 57

4S-[(1',3'-Dioxan-2'-yl)methyl]oxazolidin-2-one

Using the procedure of Example 56, replacing ethylene glycol with 1,3-propanediol gave the desired product (53%). Mass spectrum: M+ =187.

EXAMPLE 58

2S-t-Butyloxycarbonylamino-3-(1',3'-dithiolan-2'-yl)-propanol

To 360 mg of the product from Example 54 in ethanol/water (25 mL/25 mL) was added 785 mg of barium hydroxide (2 equivalents). The suspension was heated to reflux for 16 hours. Upon cooling to room temperature, the solid formed was filtered and washed with methanol. The solution was concentrated under reduced pressure. The residue was dissolved in 20 mL of dichloromethane. 1.5 equivalents of di-t-butyl-dicarbonate was added to this solution. After 2 hours, the solvent was removed under reduced pressure and the crude product was purified by silica gel column chromatography ($CH_2Cl_2$/EtOAc 6.4) to give 430 mg of pure product. Mass spectrum: M+ =279.

EXAMPLE 59

2S-t-Butyloxycarbonylamino-3-(1',3'-dithian-2'-yl)-propanol

Using 110 mg of the product from Example 55 and the procedure in Example 58 gave 90 mg of the desired product.

EXAMPLE 60

2S-Benzyloxycarbonylamino-3-(1',3'-dioxolan-2'-yl)-propanol

To 200 mg of the oxazolidinone from Example 56 in dioxane/water (15 mL/15 mL) was added 400 mg of barium hydroxide (2 equivalents). The suspension was heated to reflux for 3.5 hours, at which time all the starting material was consumed. The suspension was cooled to room temperature and filtered. The solid was washed with methanol and the solution was concentrated under reduced pressure. The residue was dissolved in 10 mL of dichloromethane and 1.5 equivalents of N-(benzyloxycarbonyloxy)-succinimide was added.

After 1 hour, the solution was concentrated under reduced pressure and the crude product was purified by silica gel column chromatography (5% MeOH/CH$_2$Cl$_2$) to give 305 mg of the desired product. Mass spectrum: M+ =281, m.p. 85°–86° C.

EXAMPLE 61

2S-Benzyloxycarbonylamino-3-(1',3'-dioxan-2'-yl)-propanol

Using 300 mg of the product from Example 57 and using the procedure of Example 76 gave 280 mg of the desired product.

EXAMPLE 62

3-hydroxy-4-t-Butyloxycarbonylamino-5-(1',3'-dithiolan-2'-yl)-pentanoic acid ethyl ester To a solution of 0.28 mL of DMSO in 15 mL of dichloromethane at −78° C. was added 0.24 mL of oxalyl chloride. After 5 minutes, a solution of 430 mg of the product from Example 65 in 20 mL of dichloromethane was added. After stirring at −78° C. for 20 minutes, 1.6 mL of triethylamine was added and the solution stirred for a further 20 minutes. It was poured into a 10% aqueous solution of potassium hydrogen sulfate. After separation of the organic phase, the aqueous phase was extracted with dichloromethane (2×100 mL). The combined organic solution was washed with water (3×50 mL) and then saturated NaCl solution and then dried with anhydrous sodium sulfate. The solution was filtered and concentrated under reduced pressure. The residual oily product as dried under high vacuum for 2 hours at room temperature. It was then dissolved in 15 mL of THF and added at −78° C. to 2.75 equivalents of lithio ethyl acetate generated in the following manner: (To 0.59 mL of diisopropyl amine in 1.5 mL of THF at −78° C. was added 1 equivalent of a hexane solution of n-butyllithium (1.6M). After 15 minutes, 0.41 mL of dry ethyl acetate was added and the solution was stirred at −78° C. for 30 minutes to ensure the complete generation of lithio ethyl acetate.) The solution was stirred at −78° C. for 20 minutes and quenched with 10% potassium hydrogen sulfate solution. The aqueous phase was extracted with ethyl acetate (3×100 mL) and the combined organic phase was dried with anhydrous MgSO$_4$. It was filtered and concentrated under reduced pressure to give a pale yellow oil which was purified by silica gel column chromatography (20% EtOAc/80% CH$_2$Cl$_2$) to give 258 mg of the desired product. Mass spectrum: M+ =365.

EXAMPLE 63

3-Hydroxy-4-t-butyloxycarbonylamino-5-(1',3'-dithian-2'-yl)-pentanoic acid ethyl ester Using the same sequence of reactions outlined in Example 62 and using 140 mg of the product from Example 59 as the starting material provided 57 mg of the desired product after silica gel column chromatography. (CH$_2$Cl$_2$/EtOAc 2:8). Mass spectrum: M+ =379.

EXAMPLE 64

3-Hydroxy-4-benzyloxycarbonylamino-5-(1',3'-dioxolan-2'-yl)-pentanoic acid ethyl ester Using the same sequence of reactions outlined in Example 62 and using 270 mg of the product from Example 60 as the starting material gave 210 mg of the desired product after silica gel column chromatography (CH$_2$Cl$_2$/EtOAc 1:1). Mass spectrum: M+ =333.

EXAMPLE 65

3-Hydroxy-4-benzyloxycarbonylamino-5-(1',3'-dioxolan-2'-yl)-pentanoic acid ethyl ester Using the same sequence of reactions outlined in Example 62 and using 274 mg of the product from Example 61 as starting material gave 200 mg of the desired product after silica gel column chromatography (CH$_2$Cl$_2$/EtOAc 6:4). Mass spectrum: M+ =347.

EXAMPLE 66

3-Hydroxy-4-t-butyloxycarbonylamino-5-(1',3'-dithiolan-2'-yl)-pentanoic acid

To a solution of 250 mg of the product from Example 62 in 6 mL of dioxane/water (1:1) was added 1.2 equivalents of lithium hydroxide. The solution was stirred at room temperature for 30 minutes. The solution was acidified with 10% potassium hydrogen sulfate solution and extracted with ethyl acetate (3×50 mL) dried with anhydrous MgSO$_4$ and filtered. The solution was concentrated under reduced pressure to afford 248 mg of a gummy white solid which is used without further purification. Mass spectrum: M+ =337.

EXAMPLE 67

3-Hydroxy-4-t-butyloxycarbonylamino-5-(1',3'-dithian-2'-yl)-pentanoic acid

Using the procedure described in Example 66 and using 50 mg of the product from Example 63 as starting material gave 49 mg of the desired product. Mass spectrum: M+ =351.

EXAMPLE 68

3-Hydroxy-4-benzyloxycarbonylamino-5-(1',3'-dioxolan-2'-yl)-pentanoic acid

Using the procedure described in Example 66 and using 200 mg of the product for Example 65 as the starting material gave 147 mg of the desired product. Mass spectrum: M+ =305.

EXAMPLE 69

3-Hydroxy-5-benzyloxycarbonylamino-5-(1',3'-dioxan-2'-yl)-pentanoic acid

Using the procedure described in Example 66 and using 200 mg of the product from Example 65 as the starting material gave 200 mg of the desired product. Mass spectrum: M+ =319.

EXAMPLE 70

3-Hydroxy-4-t-butyloxycarbonylamino-5-(1',3'-dithiolan-2'-yl)-pentanoic acid amide of 2-methylbutyl amine To a solution of 250 mg of the product from Example 66 in 30 mL of dry THF at −15° C. was added 0.13 mL of N-methylmorpholine, followed by 0.155 mL of isobutylchloro-formate. After stirring for 10 minutes, 0.25 mL of (S)-2-methylbutylamine was added. The reaction was complete after 20 minutes and was poured into 10% potassium hydrogen sulfate solution and extracted with ethyl acetate (3×50 mL), dried with anhydrous MgSO$_4$ and filtered. The solution was concentrated under reduced pressure to give a pale yellow oil which was purified by silica gel column chromatography (2% MeOH/CH$_2$Cl$_2$) to give 200 mg of pure product. Mass spectrum: M+ =406.

EXAMPLE 71

3-Hydroxy-4-t-butyloxycarbonylamino-5-(1',3'-dithian-2'-yl)-pentanoic acid amide of 2-methylbutylamine Using the procedure described in Example 70 and using 50 mg of the product from Example 67 as the starting material gave 49 mg of the desired product after silica gel column chromatography (3% MeOH/CH$_2$Cl$_2$). Mass spectrum: M+ =420.

EXAMPLE 72

3-Hydroxy-4-benzyloxycarbonylamino-5-(1',3'-dioxolan-2'-yl)-pentanoic acid amide of 2-methylbutylamine Using the procedure described in Example 70 and using 147 mg of the product from Example 68 as the starting material gave 124 mg of the desired product after silica gel column chromatography (2% MeOH/CH$_2$Cl$_2$). Mass spectrum: M+ =408.

EXAMPLE 73

3-Hydroxy-4-benzyloxycarbonylamino-5-(1',3'-dioxan-2'-yl)-pentanoic acid amide of 2-methylbutylamine Using the procedure described in Example 70 and using 200 mg of the product from Example 69 as the starting material gave 190 mg of the desired product after silica gel column chromatography (2% MeOH/CH$_2$Cl$_2$). Mass spectrum: M+ =422.

EXAMPLE 74

Amine hydrochloride of 3-hydroxy-4-t-butyloxycarbonylamino-5-(1',3'-dithiolan-2'-yl)-pentanoic acid amide of 2-methylbutylamine To 0.2 g of the product from Example 70 was added 8 mL of 4N HCl in dioxane. The solution was stirred at room temperature for 30 minutes and the solvent was then removed under reduced pressure to give a gummy solid which was used without further purification.

EXAMPLE 75

Amine hydrochloride of 3-hydroxy-4-t-butyloxycarbonylamino-5-(1',3'-dithian-2'-yl)-pentanoic acid amide of 2-methylbutylamine Using the procedure described in Example 74 and using the product from Example 71 gave the desired product which was used without further purification.

EXAMPLE 76

3-Hydroxy-4-amino-5-(1',3'-dioxolan-2'-yl)-pentanoic acid amide of 2-methylbutylamine To 124 mg of the product from Example 72 in a 50 mL round-bottom flask was added 10 mg of 10% palladium on charcoal. To this was added carefully 10 mL of methanol. The suspension was stirred vigorously under a hydrogen atmosphere by attaching a 3-way stopcock with a hydrogen-filled balloon attached. Reaction was complete in 10 minutes as shown by the complete disappearance of the starting material on TLC analysis. The suspension was filtered and the catalyst was washed with 20 mL of methanol. The combined methanol solution was concentrated under pressure to give the desired product which was used without further purification.

EXAMPLE 77

3-Hydroxy-4-amino-5-(1',3'-dioxan-2'-yl)-pentanoic acid amide of 2-methylbutylamine Using the procedure described in Example 76 and using the product from Example 73 as the starting material gave the desired product which was used without further purification.

EXAMPLE 78

Boc-Phe-S-methylcysteinyl-[3-hydroxy-4-amino-5-(1',3'-dithiolan-2'-yl)]-pentanoic acid amide of 2-methylbutylamine To a solution of 57 mg of Boc-Phe-S-methylcysteine in 5 mL of THF at −15° C. was added 0.017 mL of N-methylmorpholine, followed by 0.020 mL of isobutylchloroformate. After 10 minutes, a solution of the product from Example 74 (starting with 49 mg) in 5 mL of THF with 0.016 mL of N-methylmorpholine was added. After the solution was stirred at −15° C. for one hour, it was poured into 10% potassium hydrogen sulfate and extracted with ethyl acetate (3×50 mL), dried with anhydrous MgSO$_4$ and filtered. The solvent was evaporated under reduced pressure. The crude product obtained was purified by silica gel column chromatography (CH$_2$Cl$_2$/EtOAc 3:7) to give 36 mg of product. Mass spectrum: (M+H)+ =671; m.p.=144°–145° C.

EXAMPLE 79

Boc-Phe-S-methylcysteinyl-[3-hydroxy-4-amino-5-(1',3'-dithian-2'-yl)]-pentanoic acid amide of 2-methylbutylamine Using the procedure described in Example 78, and using 57 mg of Boc-Phe-S-methyl-cysteine and the product from Example 75 (from 44 mg of starting material) gave 25 mg of the desired product after silica gel column chromatography (CH$_2$Cl$_2$/EtOAc 3:7). Mass spectrum: (M+H)+ =685.

EXAMPLE 80

Boc-Phe-S-methylcysteinyl-[3-hydroxy-4-amino-5-(1',3'-dioxolan-2'-yl)]-pentanoic acid amide of 2-methylbutylamine Using the procedure described in Example 78 and using 63 mg of Boc-Phe-S-methyl-cysteine, 40 mg of the product from Example 76, gave 51 mg of the desired product after silica gel column chromatography (2% MeOH/CH$_2$Cl$_2$). Mass spectrum: (M+H)+ =639.

EXAMPLE 81

Boc-Phe-S-methylcysteinyl-[3-hydroxy-4-amino-5-(1',3'-dioxan-2'-yl)]-pentanoic acid amide of 2-methylbuylamine Using the procedure described in Example 78, and using 40 mg of Boc-Phe-S-methyl-cysteine, 40 mg of the product from Example 77 gave 40 mg of the desired product after silica gel column chromatography (2% MeOH/CH$_2$Cl$_2$). Mass spectrum: (M+H)+ =653.

EXAMPLE 82

Ethoxycarbonyl-Phe-Leu-[3-hydroxy-4-amino-5-(1',3'-dioxan-2'-yl)]-pentanoic acid amide of 2-methylbutylamine Using the procedure described in Example 78, and using 42 mg of the ethoxycarbonyl-Phe-Leu, 35 mg of the product from Example 77 gave 36 mg of product after silica gel column chromatography (2% MeOH/CH$_2$Cl$_2$). Mass spectrum: (M+H)+ =621.

EXAMPLE 83

Boc-Phe-His-[3-hydroxy-4-amino-5-(1',3'-dithiolan-2'-yl)]-pentanoic acid amide of 2-methylbutylamine To a solution of 47 mg of Boc-Phe-His-OH in 5 mL of DMF at −15° C. was added sequentially 45 mg of 1-hydroxybenzotriazole, 21 mg of ethyl dimethylaminopropyl carbodiimide. After 1 hour at −15° C., a solution of 37 mg of the product from Example 74 in 3 mL of DMF was added. The solution was kept at −15° C. for several hours and then at room temperature overnight. The solvent was removed under reduced pressure and the residue was washed with saturated sodium bicarbonate and extracted with ethyl acetate (3×50 mL), dried with anhydrous MgSO$_4$ and filtered. The solution was concentrated under reduced pressure and the crude product was purified by silica gel column chromatography (5% MeOH/CH$_2$Cl$_2$) to give 12 mg of product. Mass spectrum: (M+H)+ =691.

EXAMPLE 84

2(R,S)-(4-morpholinylcarbonylmethyl)-3-(1'-naphthyl)-propionic Acid

To 50 ml of absolute ethanol was added 2 g of sodium metal. The suspension was stirred vigorously until all the sodium dissolved and the evolution of hydrogen ceased. To this solution of sodium ethoxide was added a solution of 11.6 g of diethylsuccinate in 10.4 g of 1-naphthaldehyde. The solution was heated to reflux for 3 h, at which time it was cooled to room temperature and concentrated on the rotavap. The residue was dissolved in 320 ml of water and extracted 6 times with 100 ml portions of ether. The aqueous layer was acidified with 2N HCl and extracted with 2×300 ml of ether and dried with anhydrous magnesium sulfate. Evaporation of the solvent gave a yellow gummy solid which was hydrogenated to the saturated acid using Pd/C as catalyst. Coupling of the resulting saturated acid to morpholine using the mixed anhydride method described in Example 17 followed by ester hydrolysis using the procedure of Example 2 gave the desired acid. Mass spectrum: (M+H)+ =328.

EXAMPLE 85

Boc-ACHPA-amide of 2-methylbutylamine

Using the procedure of Example 3, but replacing Boc-Sta with Boc-ACHPA and benzylamine with 2-methylbutylamine gave the desired compound (76% yield). Mass spectrum: M+ =384.

EXAMPLE 86

Boc-His-ACHPA-amide of 2-methylbutylamine

Using the procedure of Example 10, but using the amine hydrochloride of Boc-ACHPA-amide of 2-methylbutylamine and replacing Boc-Phe-His with Boc-His-OH gave the desired compound (62% yield). Mass spectrum: (M+H)+ =522.

EXAMPLE 87

2(R,S)-(4-morpholinylcarbonylmethyl)-3-(1'-naphthyl)-propionyl-His-ACHPA-amide of 2-methylbutylamine Using the procedure of Example 10, but replacing Boc-Phe-His-OH with the product in Example 84, and using the amine hydrochloride of Example 86 gave the desired product (65% yield). Mass spectrum: (M+H)+ =719.

EXAMPLE 88

2(R,S)-(4-morpholinylcarbonylmethyl)-3-(4'-methoxyphenyl)-propionic Acid

Using the procedure described in Example 84, but replacing 1-naphthaldehyde with anisaldehyde gave the desired compound. Mass spectrum: M+ =295.

EXAMPLE 89

2(R,S)-(4-morpholinylcarbonylmethyl)-3-(4'-methoxyphenyl)-propionyl-His-ACHPA-amide of 2-methylbutylamine Using the procedure of Example 10, but replacing Boc-Phe-His-OH with the product in Example 88, and using the amine hydrochloride of Example 86 gave the desired product (61% yield). Mass spectrum: (M+H)+ =699.

EXAMPLE 90

(3,4-cis-dihydroxypyrrolidinylcarbonyl)-Phe-methyl Ester

A suspension of L-phenylalanine methyl ester hydrochloride (10 g) in toluene (200 ml) was heated to 100° C. while phosgene gas was bubbled into the reaction mixture. After approximately 2 h the mixture became homogeneous. The bubbling of phosgene was continued for 15 more minutes keeping the temperature at 100° C. The toluene was then evaporated and the residue chased with benzene several times. The isocyanate from L-Phe-OCH$_3$ was then dissolved in 100 ml of methylene chloride and 1.1 equivalent of 3-pyrroline (75% pure) was added dropwise at 0° C. After 15 min, the reaction mixture was washed with 0.5N HCl and methylene chloride. The organic layer was washed with aqueous NaHCO$_3$ and dried over MgSO$_4$. Evaporation of the solvent gave 3-pyrrolinylcarbonyl-Phe-methyl ester which was cis-hydroxylated under the following conditions: 2.5 g of the 3-pyrrolinylcarbonyl-Phe-methyl ester was dissolved in 50 ml of THF and 1 ml of a 2.5% solution of OsO$_4$ in t-butanol was added, followed by 1.15 g of N-methylmorpholine-N-oxide. After 1 h, the solvent was evaporated and the residue dissolved in 150 ml of ethyl acetate and washed with dilute Na$_2$SO$_3$ solution, satd. NaHCO$_3$ solution and then dried with MgSO$_4$. Evaporation of the solvent gave a gummy solid which was purified by SiO$_2$ column chromatography (5% MeOH/CH$_2$Cl$_2$) to give the desired compound (65% yield). Mass spectrum: M+ =308.

EXAMPLE 91

(3,4-cis-dihydroxypyrrolidinylcarbonyl)-Phe-OH

Using the procedure of Example 2 and replacing Boc-Sta-OEt with the product from Example 90 gave the desired compound. Mass spectrum: M+ =294.

EXAMPLE 92

(3,4-cis-dihydroxypyrrolidinylcarbonyl)-O-methyl-Tyr-methyl Ester

Using the procedure described in Example 90 and replacing L-phenylalanine methyl ester with L-O-methyltyrosine methyl ester gave the desired compound. Mass spectrum: M+ =338.

EXAMPLE 93

(3,4-cis-dihydroxypyrrolidinylcarbonyl)-O-methyl-Tyr-OH

Using the procedure described in Example 2 and replacing Boc-Sta-OEt with the product from Example 92 gave the desired compound. Mass spectrum: $M^+ = 324$.

EXAMPLE 94

Boc-S-methyl-cys-ACHPA-amide of 2-Methylbutylamine

Using the procedure described in Example 11, but replacing Boc-(α-Naphthyl)-Ala-Ala-OH with Boc-S-methyl-Cys-OH and using the amine hydrochloride of the product from Example 85 gave the desired compound. Mass spectrum: $(M+H)^+ = 502$.

EXAMPLE 95

(3,4-cis-dihydroxypyrrolidinylcarbonyl)-Phe-S-methyl-cys-ACHPA-amide of 2-Methylbutylamine Using the procedure described in Example 11 but replacing Boc(α-Naphthyl)-Ala-Ala-OH with the product from Example 91 and the amine hydrochloride of the compound from Example 94 gave the desired compound. Mass spectrum: $(M+H)^+ = 678$.

EXAMPLE 96

Boc-O-methyl-Ser-ACHPA-amide of 2-Methylbutylamine

Using the procedure described in Example 11, but replacing Boc-(α-Naphthyl)-Ala-Ala-OH with Boc-O-methyl-Ser-OH and using the amine hydrochloride of the product from Example 85 gave the desired compound. Mass spectrum: $(M+H)^+ = 486$.

EXAMPLE 97

(3,4-cis-dihydroxypyrrolidinylcarbonyl)-O-methyl-Tyr-O-methyl-Ser-ACHPA Amide of 2-Methylbutylamine Using the procedure described in Example 11, but replacing Boc-(α-Naphthyl)-Ala-Ala-OH with the product from Example 93 and using the amine hydrochloride of the compound from Example 96 gave the desired compound. Mass spectrum: $(N+H)^+ = 682$.

EXAMPLE 98

[(4-Thiomorpholinyl)carbonyl]-Phe Methyl Ester

A suspension of L-phenylalamine methyl ester hydrochloride (6 g) in toluene (125 ml) was heated to 100° C. and phosgene gas was bubbled into the reaction mixture. After approximately 1.5 h, the mixture became homogeneous. The bubbling of phosgene was continued for 10 more min. The solvent was then evaporated and the residue chased with benzene several times. The residue was then dissolved in 100 ml of methylene chloride and cooled to 0° C., and 1.1 equivalent of thiomorpholine was added dropwise. After 10 min the solution was washed with 1N HCl and the organic layer was dried with MgSO4. Evaporation of solvent gave 5.5 g of product. Mass spectrum: $M^+ = 308$.

EXAMPLE 99

[(4-Sulphonylmorpholinyl)carbonyl]-Phe Methyl Ester

To 2 g of the product from Example 98 i 100 ml of methylene chloride was added 2.94 g of a meta-chloroperbenzoic acid at 0° C. After 30 min the solvent was evaporated and ether solution was washed with 10% sodium sulfite solution and then with satd. sodium bicarbonate several times. The organic layer was dried with MgSO4 and evaporation of the solvent gave a white solid which was purified by silica gel column chromatography (20% EtOAc/80%/CH2Cl2) to give 2.10 g (95%) of pure product. Mass spectrum: $M^+ = 340$.

EXAMPLE 100

[(4-sulfonylmorpholinyl)carbonyl]-Phe-OH

Using the procedure described in Example 2, but replacing Boc-Sta-OEt with the product from Example 99 gave the desired compound.

EXAMPLE 101

[(4-sulfonylmorpholinyl)carbonyl]-Phe-O-methyl-Ser-ACHPA-amide of 2-Methylbutylamine Using the procedure described in Example 11, but replacing Boc-(α-Naphthyl)-Ala-Ala-OH with the product from Example 100 and using the amine hydrochloride of the product from Example 96 gave the desired compound (70% yield). Mass spectrum: $(M+H)^+ = 694$.

EXAMPLE 102

4-t-Butyloxycarbonylamino-2,2-difluoro-3-hydroxy-5-cyclohexylpentanoic acidethyl ester To a solution of 8.0 g of Boc-cyclohexylalaninal in 125 ml of tetrahydrofuran at 10° C. was added 10 ml of ethyl bromodifluoroacetate. The reaction flask was immersed in a sonicating bath. To this solution was added portionwise 6.18 g of zinc duct. After 30 min of sonication TLC check showed reaction was essentially complete. The reaction mixture was filtered through a tightly packed pad of Celite and the filtrate was concentrated. The residual oil was dissolved in methylene chloride and washed with 0.5M potassium bisulfate. The organic layer was dried with anhydrous sodium sulfate, filtered and concentrated. Purification by silica gel column (20% ethyl acetate/80% hexane) provided 4.5 g of 3R isomer and 4.0 g of 3S isomer. Mass spectrum: $M^+ = 379$.

EXAMPLE 103

4(S)-t-butyloxycarbonylamino-2,2-difluoro-3R-hydroxy-5-cyclohexylpentanoic acid

Using the procedure of Example 2, but replacing Boc-Sta-OEt with the product from Example 102 gave the desired product. Mass spectrum: $M^+ = 351$.

EXAMPLE 104

4S-t-butyloxycarbonylamino-2,2-difluro-3R-hydroxy-5-cyclohexylpentanoic acid amide of 2-methylbutylamine Using the procedure of Example 3, but replacing Boc-Sta-OH with the product from Example 103 and replacing benzyl amine with 2-methylbutylamine gave the desired product (75% yield). Mass spectrum: $M^+ = 420$.

EXAMPLE 105

Boc-Phe-His-4S-amino-2,2-difluoro-3R-hydroxy-5-cyclohexylpentanoic acid amide of 2-methylbutylamine Using the procedure of Example 10, but using the amine hydrochloride of the product in Example 104 gave the desired product (47% yield). Mass spectrum: $(M+H)^+ = 705$.

The compounds of the present invention can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, dodecylsulfate, cyclopentanepropionate, digluconate, ethanesulfonate, fumarate, glucoheptanoate, glycerophosphate, hexanoate, hemisulfate, heptonate, hydrochloride, hydrobromide, hydroiodide, 2-hydroxy-ethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, undecanoate, and tosylate. Also, the basic nitrogen-containing groups can be quaternized with such agents as loweralkyl halides, such as methyl, ethyl, propyl and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The novel compounds of the present invention possess an excellent degree of activity and specificity in treating renin-associated hypertension in a host. The ability of the compounds of the invention to inhibit human renal renin can be demonstrated in vitro by reacting a selected compound at varied concentrations with human renal renin, free from acid proteolytic activity, and with human renin substrate (angiotensinogen) at 37° C. and pH 6.0. At the end of the incubation, the amount of angiotensin I formed is measured by radioimmunoassay and the molar concentration required to cause 50% inhibition, expressed as the $IC_{50}$, is calculated. When tested in accordance with the foregoing procedure, the compounds of the invention demonstrated $IC_{50}$'s in the range of $10^{-5}$ to $10^{-10}$M as seen in Table I.

TABLE I

| Example | Activity -$IC_{50}$ (M) |
|---|---|
| 10 | $7 \times 10^{-7}$ |
| 11 | $4 \times 10^{-7}$ |
| 12 | $5 \times 10^{-7}$ |
| 13 | $5 \times 10^{-8}$ |
| 16 | $1 \times 10^{-7}$ |
| 17 | $1 \times 10^{-6}$ |
| 25 | $5 \times 10^{-9}$ |
| 32 | $6 \times 10^{-9}$ |
| 33 | $3.5 \times 10^{-8}$ |
| 34 | $2 \times 10^{-8}$ |
| 35 | $7 \times 10^{-9}$ |
| 40 | $3 \times 10^{-8}$ |
| 45 | $1 \times 10^{-9}$ |
| 46 | $1.5 \times 10^{-9}$ |
| 47 | $1 \times 10^{-9}$ |
| 48 | $7 \times 10^{-10}$ |
| 49 | $1.5 \times 10^{-9}$ |
| 50 | $1 \times 10^{-9}$ |
| 78 | $1 \times 10^{-9}$ |
| 79 | $6 \times 10^{-9}$ |
| 80 | $6 \times 10^{-7}$ |

TABLE I-continued

| Example | Activity -$IC_{50}$ (M) |
|---|---|
| 81 | $7 \times 10^{-7}$ |
| 82 | $7.5 \times 10^{-6}$ |
| 83 | $1.5 \times 10^{-9}$ |
| 87 | $2 \times 10^{-9}$ |
| 89 | $6.1 \times 10^{-8}$ |
| 95 | $5.6 \times 10^{-10}$ |
| 97 | $1.6 \times 10^{-8}$ |

Total daily dose administered to a host in single or divided doses may be in amounts, for example, from 0.001 to 10 mg/kg body weight daily and more usually 0.01 to 1 mg. Dosage unit compositions may contain such amounts or submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of the present invention may be administered orally, parenterally, by inhalation spray, rectally or topically in dosage unit formulations containing conventional nontoxic pharmaceutically acceptable carriers, adjuvants and vehicles as desired. The term parenteral as used herein includes subcutaneous injections, intravenous, intramuscular, intrasternal injection or infusion techniques.

Injectable preparations, for example, sterile injectable aqueous or oleagenous suspensions may be formulated according to the known art using suitable dispersing of wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

Suppositories for rectal administration of the drug can be prepared by mixing the drug with a suitable nonirritating excipient such as cocoa butter and polyethylene glycols which are solid at ordinary temperatures but liquid at the rectal temperature and will therefor melt in the rectum and release the drug.

Solid dosage forms for oral administration may include capsules, tablets, pills, powders and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration may include pharmaceutically acceptable emulsions, syrups, solutions, suspensions and elixirs containing inert diluents commonly used in the art, such as water. Such compositions may also comprise adjuvants, such as wetting agents, emulsifying and suspending agents, and sweetening, flavoring and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

We claim:

1. A compound of the formula

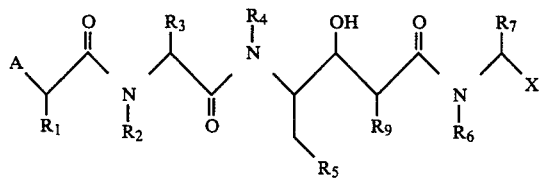

wherein A is

wherein B is thiomorpholino, morpholino, 4-sulfonylmorpholino, 3,4-dihydroxypyrrolidino, alkoxy or loweralkyl and C is NH or $CH_2$; $R_1$, $R_3$ and $R_7$ are independently selected from loweralkyl or lipophilic or aromatic amino acid side chains; $R_2$, $R_4$, and $R_6$ are independently selected from hydrogen or loweralkyl; $R_5$ is phenyl, isopropyl, cyclohexyl, 1,3 dioxan-2-yl; 1,3-dioxolan-2-yl, loweralkyl, 1,3-dithiolan-2-yl or 1,3-dithian-2-yl; X is hydrogen, loweralkyl or $-CH_2OR_8$, wherein $R_8$ is hydrogen, loweralkyl or alkaryl; and $R_9$ is hydrogen, loweralkyl, hydroxy, hydroxyalkyl, difluoro, alkoxy, allyl, alkaryloxy or thioalkyl and pharmaceutically acceptable salts thereof.

2. The compound of claim 1 wherein $R_2$, $R_4$, and $R_6$ are hydrogen.

3. The compound of claim 2 wherein X is hydrogen.

4. The compound of claim 3 wherein B is t-butyloxy or ethoxy and C is NH.

5. The compound of claim 4 wherein $R_9$ is hydrogen, methoxy, propyl, allyl or difluoro.

6. The compound of claim 5 wherein $R_1$ is benzyl, α- or β-naphthylmethyl or p-methoxybenzyl; $R_3$ is methyl, methylthiomethyl, imidazole-4-yl-methyl or methylthioethyl; $R_5$ is isopropyl, cyclohexyl, phenyl, 1,3-dithiolan-2-yl, 1,3-dioxolan-2-yl, 1,3-dithian-2-yl or 1,3-dioxan-2-yl; and $R_7$ is loweralkyl or imidazole-4-yl-methyl.

7. The compound of claim 6 wherein $R_1$ is benzyl, $R_3$ is methylthiomethyl, $R_5$ is cyclohexyl, $R_7$ is isopropyl, $R_9$ is methoxy and B is t-butyloxy.

8. The compound of claim 6 wherein $R_1$ is benzyl, $R_3$ is methylthiomethyl or imidazole-4-yl-methyl, $R_5$ is 1,3-dithiolan-2-yl, $R_7$ is isobutyl, $R_9$ is hydrogen and B is t-butyloxy.

9. A pharmaceutical composition for treating renin-associated hypertension, comprising a pharmaceutical carrier and a therapeutically effective amount of the compound of claim 1.

10. A method of treating hypertension comprising administering to a host in need of such treatment a therapeutically effective amount of a compound of claim 1.

* * * * *

UNITED STATES PATENT AND TRADEMARK OFFICE
CERTIFICATE OF CORRECTION

PATENT NO. : 4,826,958

DATED : May 2, 1989

INVENTOR(S) : Hing L. Sham

It is certified that error appears in the above-identified patent and that said Letters Patent is hereby corrected as shown below:

Column 2, line 47: Replace "1,3-di-thian" with --1,3-dithian--

Column 11, line 32: Replace "4-Hydroxyethyl" with --4S-Hydroxyethyl--

Column 14, line 47: Replace "3-Hydroxy-5-benzyloxycarbonylamino" with --3-Hydroxy-4-benzyloxycarbonylamino--

Column 24, lines 29 and 30: Delete "renin-associated"

Signed and Sealed this

Twelfth Day of February, 1991

Attest:

HARRY F. MANBECK, JR.

Attesting Officer     Commissioner of Patents and Trademarks